(12) United States Patent
Ballantyne et al.

(10) Patent No.: US 10,871,889 B2
(45) Date of Patent: *Dec. 22, 2020

(54) TELE-PRESENCE SYSTEM WITH A USER INTERFACE THAT DISPLAYS DIFFERENT COMMUNICATION LINKS

(71) Applicant: INTOUCH TECHNOLOGIES, INC., Goleta, CA (US)

(72) Inventors: James Ballantyne, Santa Barbara, CA (US); Kelton Temby, Santa Barbara, CA (US); James Rosenthal, Santa Barbara, CA (US); David Roe, Santa Barbara, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/450,842

(22) Filed: Jun. 24, 2019

(65) Prior Publication Data

US 2020/0142576 A1 May 7, 2020

Related U.S. Application Data

(60) Continuation of application No. 15/658,273, filed on Jul. 24, 2017, now Pat. No. 10,331,323, which is a
(Continued)

(51) Int. Cl.
| | |
|---|---|
| *G06F 3/0484* | (2013.01) |
| *A61B 34/00* | (2016.01) |
| *G06F 19/00* | (2018.01) |
| *H04N 7/14* | (2006.01) |
| *G16H 40/63* | (2018.01) |
| *A61B 5/00* | (2006.01) |

(Continued)

(52) U.S. Cl.
CPC ........ *G06F 3/04847* (2013.01); *A61B 5/7465* (2013.01); *A61B 34/25* (2016.02); *G06F 3/04817* (2013.01); *G06F 3/04842* (2013.01); *G06F 3/1454* (2013.01); *G06F 19/3418* (2013.01); *G16H 40/63* (2018.01); *G16H 40/67* (2018.01); *H04N 7/142* (2013.01); *H04N 7/148* (2013.01)

(58) Field of Classification Search
CPC ............... G06F 3/04847; G06F 3/1454; G06F 3/04842; G06F 3/04817; A61B 34/25; A61B 5/7465; G16H 40/67; G16H 40/63; H04N 7/148; H04N 7/142
See application file for complete search history.

(56) References Cited

U.S. PATENT DOCUMENTS

| | | | |
|---|---|---|---|
| 9,715,337 B2 * | 7/2017 | Ballantyne | G16H 40/67 |
| 10,331,323 B2 * | 6/2019 | Ballantyne | H04N 7/148 |
| 2010/0081430 A1 * | 4/2010 | Rofougaran | H04W 76/15 |
| | | | 455/426.1 |

* cited by examiner

*Primary Examiner* — Stella L. Woo

(57) ABSTRACT

A tele-presence system that includes a remote device coupled to a control station through a communication link. The remote device includes a remote monitor, a remote camera, a remote speaker and a remote microphone. Likewise, the control station includes a station monitor, a station camera, a station speaker and a station microphone. The control station displays a plurality of graphical icons that each represents a different type of communication link between the control station and the remote device. The graphical icons can be selected to allow a user of the control station to change the communication link between the remote device and its initial node.

12 Claims, 11 Drawing Sheets

Related U.S. Application Data continuation of application No. 14/454,686, filed on Aug. 7, 2014, now Pat. No. 9,715,337, which is a division of application No. 13/291,912, filed on Nov. 8, 2011, now Pat. No. 8,836,751.

(51) Int. Cl.
*G06F 3/0481* (2013.01)
*G06F 3/14* (2006.01)
*G16H 40/67* (2018.01)

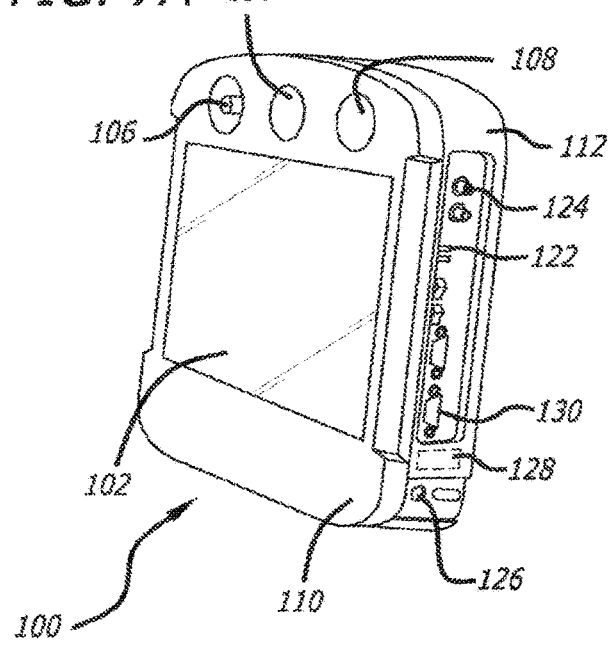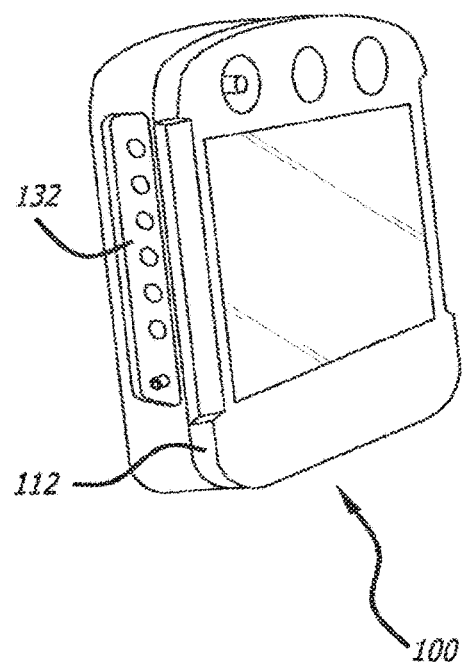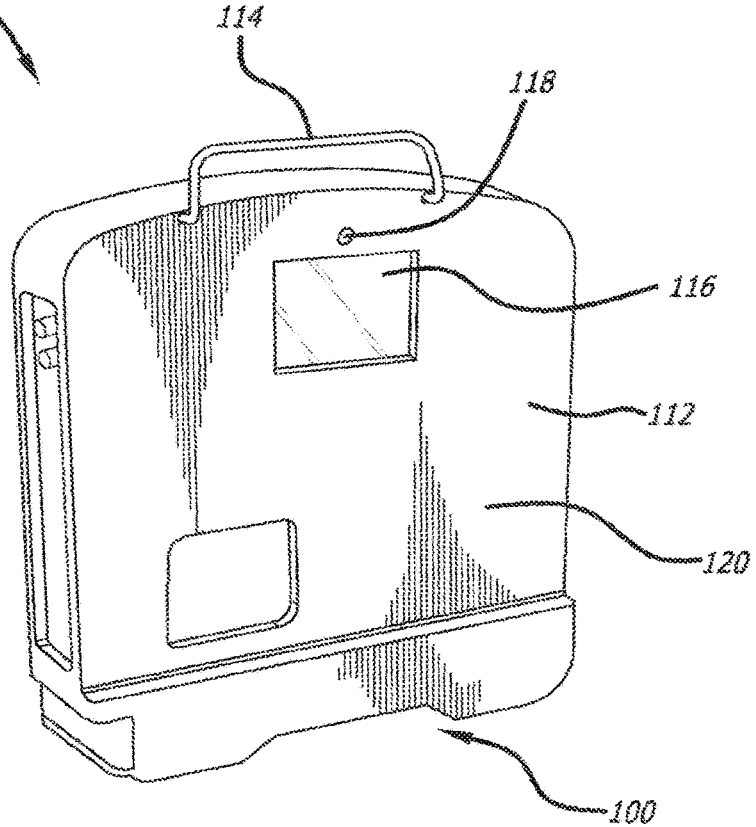

TELE-PRESENCE SYSTEM WITH A USER INTERFACE THAT DISPLAYS DIFFERENT COMMUNICATION LINKS

BRIEF DESCRIPTION OF THE DRAWINGS

FIGS. 7A and 7B are illustrations of an alternate embodiment of the robot face;

FIG. 8 is an illustration of a rear view of the robot face shown in FIG. 7;

DETAILED DESCRIPTION

Disclosed is a tele-presence system that includes a remote device coupled to a control station through a communication link. The remote device includes a remote monitor, a remote camera, a remote speaker and a remote microphone. Likewise, the control station includes a station monitor, a station camera, a station speaker and a station microphone. The control station displays a plurality of graphical icons that each represents a different type of communication link between the remote device and its initial node. The graphical icons can be selected to allow a user of the control station to change that communication link.

Figure 1:
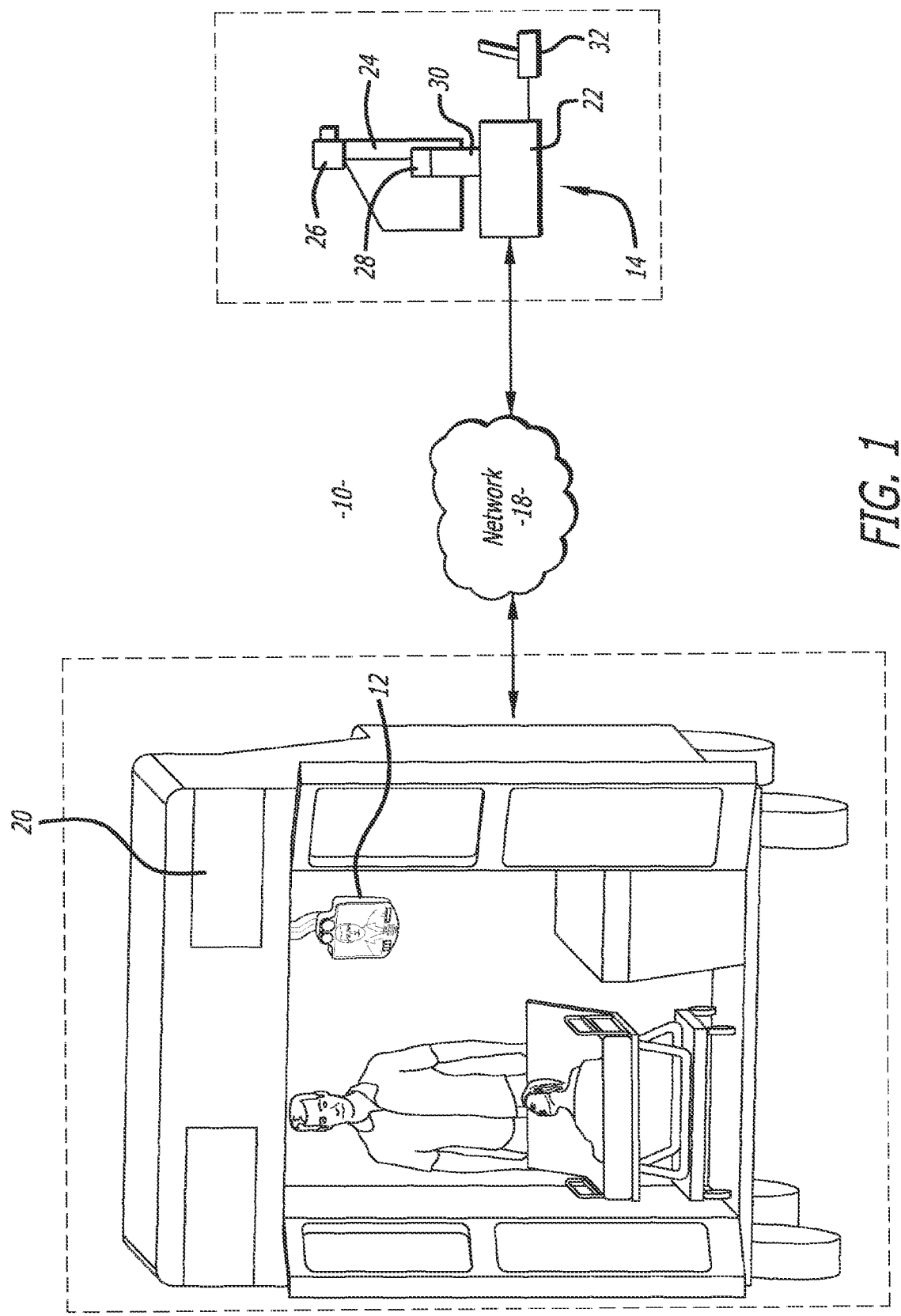
FIG. 1 is an illustration of a tele-presence system that includes a remote station coupled to a portable robot face located within an ambulance.

Referring to the drawings more particularly by reference numbers, FIG. 1 shows a tele-presence system 10. The system 10 includes a remote device 12 that is coupled to a remote control station 14 through a network 18. The remote device may be a portable robot face, such as the robot face sold by the assignee of the present application, InTouch Technologies, Inc. under the product name RP-Xpress. The remote device 12 may also be a mobile robot such as the robot sold by InTouch Technologies, Inc. under the product name RP-7. The network may be wired system, or a wireless system such as a cellular broadband network and/or a WiFi network. The portable robot face 12 is shown located within an ambulance 20.

The remote control station 14 may include a computer 22 that has a monitor 24, a camera 26, a microphone 28 and a speaker 30. The computer 22 may also contain an input device 32 such as a joystick or a mouse. The control station 14 is typically located in a place that is remote from the remote device. Although only one remote control station 14 is shown, the system 10 may include a plurality of remote stations 14. In general any number of remove devices 12 may be coupled to any number of remote stations 14 or other remote devices 12. For example, one remote station 14 may be coupled to a plurality of remote devices 12, or one remote device 12 may be coupled to a plurality of remote stations 14, or a plurality of remote devices 12. The system may include an arbitrator (not shown) that controls access between the remote device(s) 12 and the remote stations 14.

Figure 2:
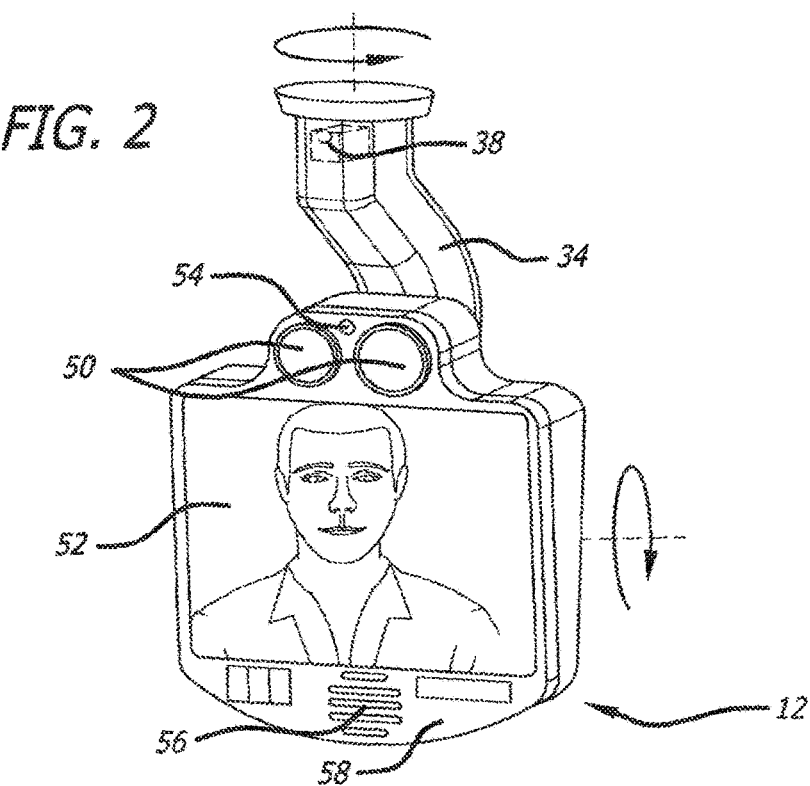
FIG. 2 is an illustration showing the portable robot face within the ambulance.
Figure 3:
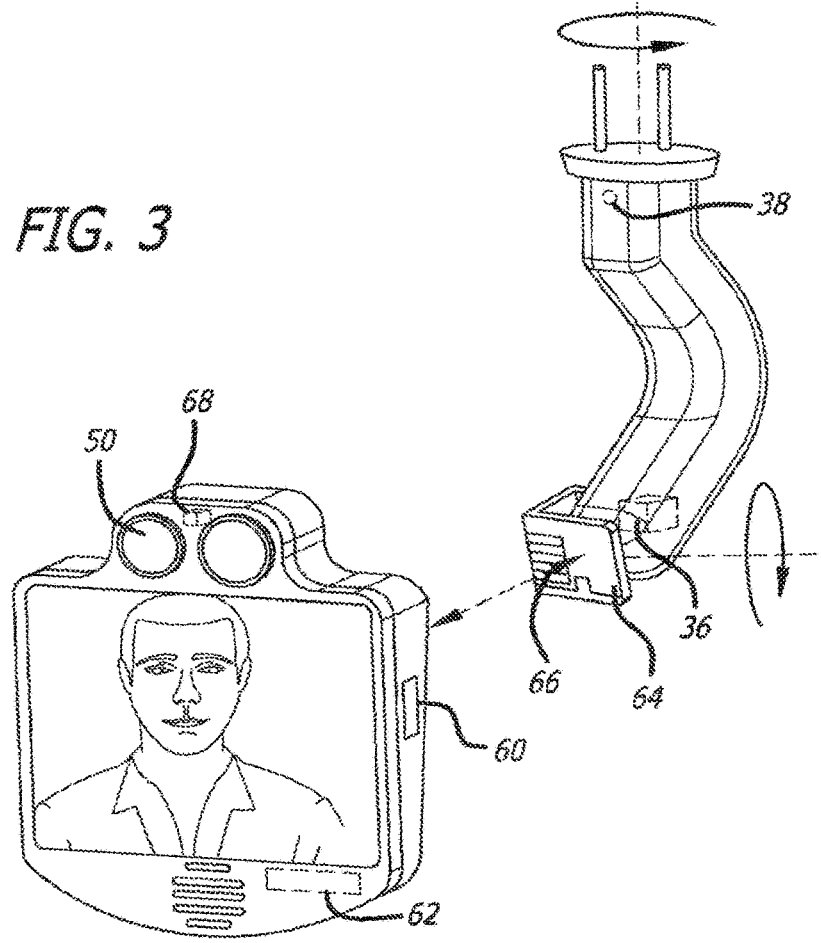
FIG. 3 is an illustration showing the portable robot face detached from a platform mounted to the ambulance ceiling.

As shown in FIGS. 2 and 3, a portable robot face 12 may be attached to a platform 34. The platform 34 may extend from the ceiling (not shown) of the ambulance 20. The platform 34 may include articulate joints 36 and 38 that provide at least two degrees of freedom and allow a user to move the robot face 12 to different positions to view a patient and an EMT within the ambulance.

Each robot face 12 includes a camera(s) 50, a monitor 52, a microphone(s) 54 and a speaker(s) 56 that are all attached to a housing 58. The robot camera 50 is coupled to the remote monitor 24 so that a user at the remote station 14 can view the patient and/or EMT. Likewise, the robot monitor 52 is coupled to the remote camera 26 so the patient and EMT may view the user of the remote station 14. The microphones 28 and 54, and speakers 30 and 56, allow for audible communication between the system operator and the patient and/or EMT.

The system 10 allows a system user such as a physician to view a patient in the ambulance and provide remote medical consultation through the remote station 14 and the robot face 12. Personnel such as the EMT can transmit questions and responses through the system back to the physician. The robot camera 50 allows the physician to view the patient and enhance the medical consultation. The robot monitor 52 can display the physician to provide a feeling of presence in the ambulance. The platform 34 allows the physician to pan and tilt the robot face 12.

The robot face 12 may include a wireless transceiver 60 that is coupled to the wireless network. The portable face 12 also includes a battery 62.

The system 10 may have certain components and software that are the same or similar to robotic systems provided by the assignee InTouch Technologies, Inc. of Goleta, Calif. under the names RP-Xpress and RP-7, and embodies a system described in U.S. Pat. No. 6,925,357, which is hereby incorporated by reference.

As shown in FIG. 3, the portable robot face 12 can be detached from the platform 34. The robot face 12 and platform 34 may have mechanical connectors 64 that allow the face 12 to be readily attached and detached from the platform 34. Likewise, the robot face 12 and platform 34 may include electrical connectors 66. The ambulance may include a wireless transceiver (not shown) that can provide wireless communication to the remote station. The electrical connectors 66 provide an electrical connection between the robot face 12 and the ambulance wireless transceiver. The connectors 66 may also provide power to the robot face 12. Alternatively, the wireless transceiver 60 of the robot face 12 may be coupled to the remote station through the ambulance wireless transceiver. The robot face may include an actuator system 68 that can move the camera 50 in two degrees of freedom. This allows the operator to move the camera field of view even when the face 12 is detached from the platform 34.

Figure 4:
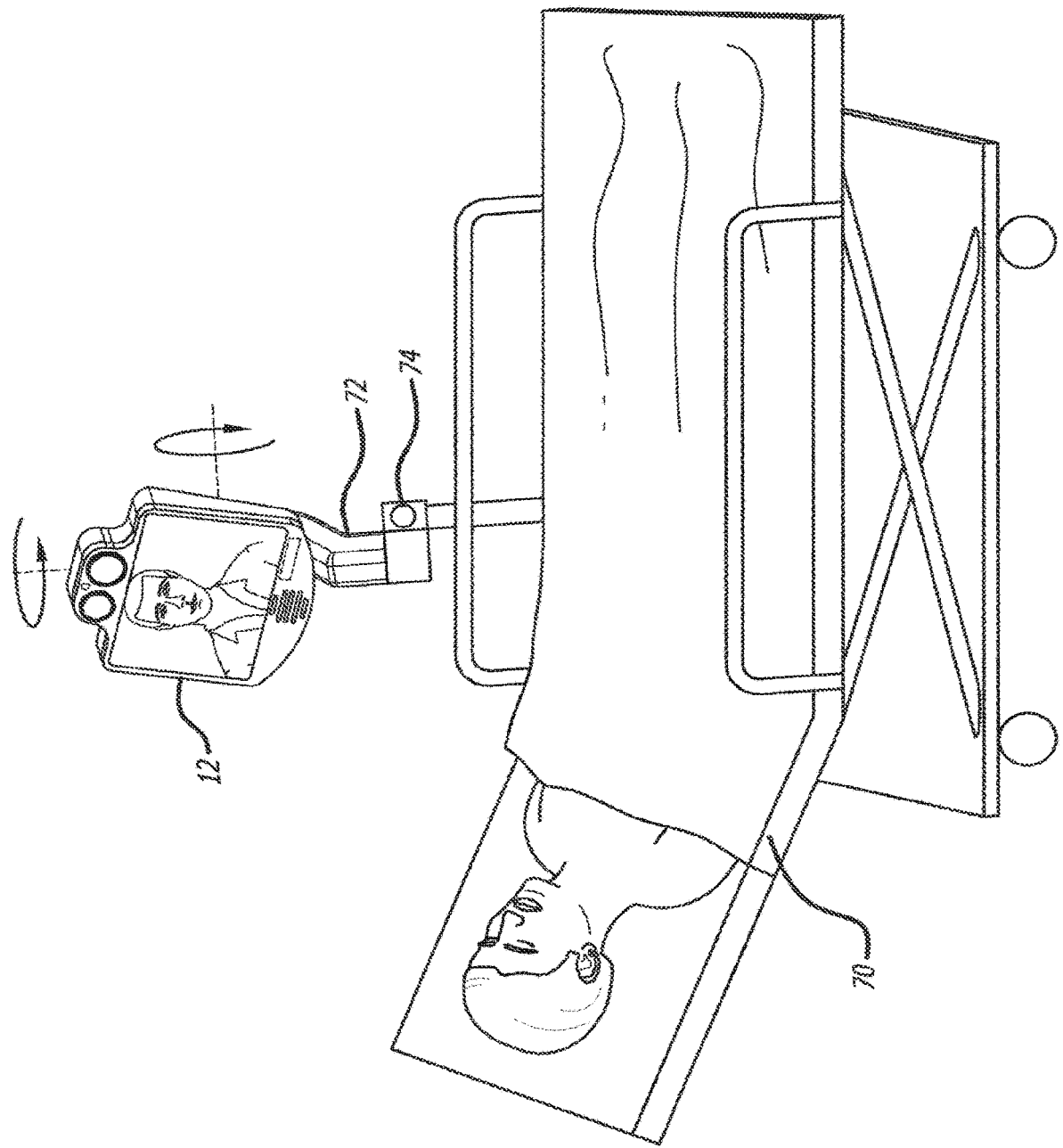
FIG. 4 is an illustration showing the portable robot face attached to a patient gurney.

As shown in FIG. 4 the portable robot face 12 can be detached from the platform (not shown) and attached to the patient gurney 70. The robot face 12 may be attached to a platform 72 with two degrees of freedom that allow the remote station user to move the robot face 12. The platform 72 may include a clamp 74 that allows for attachment to the gurney 70. The robot face 12 and patient can be moved out of the ambulance on the gurney 70. The portable aspect of the robot face 12 allows the face to be moved with the patient. The robot face 12 should be of a size and weight so that an individual can lift the face 12.

Figure 5:
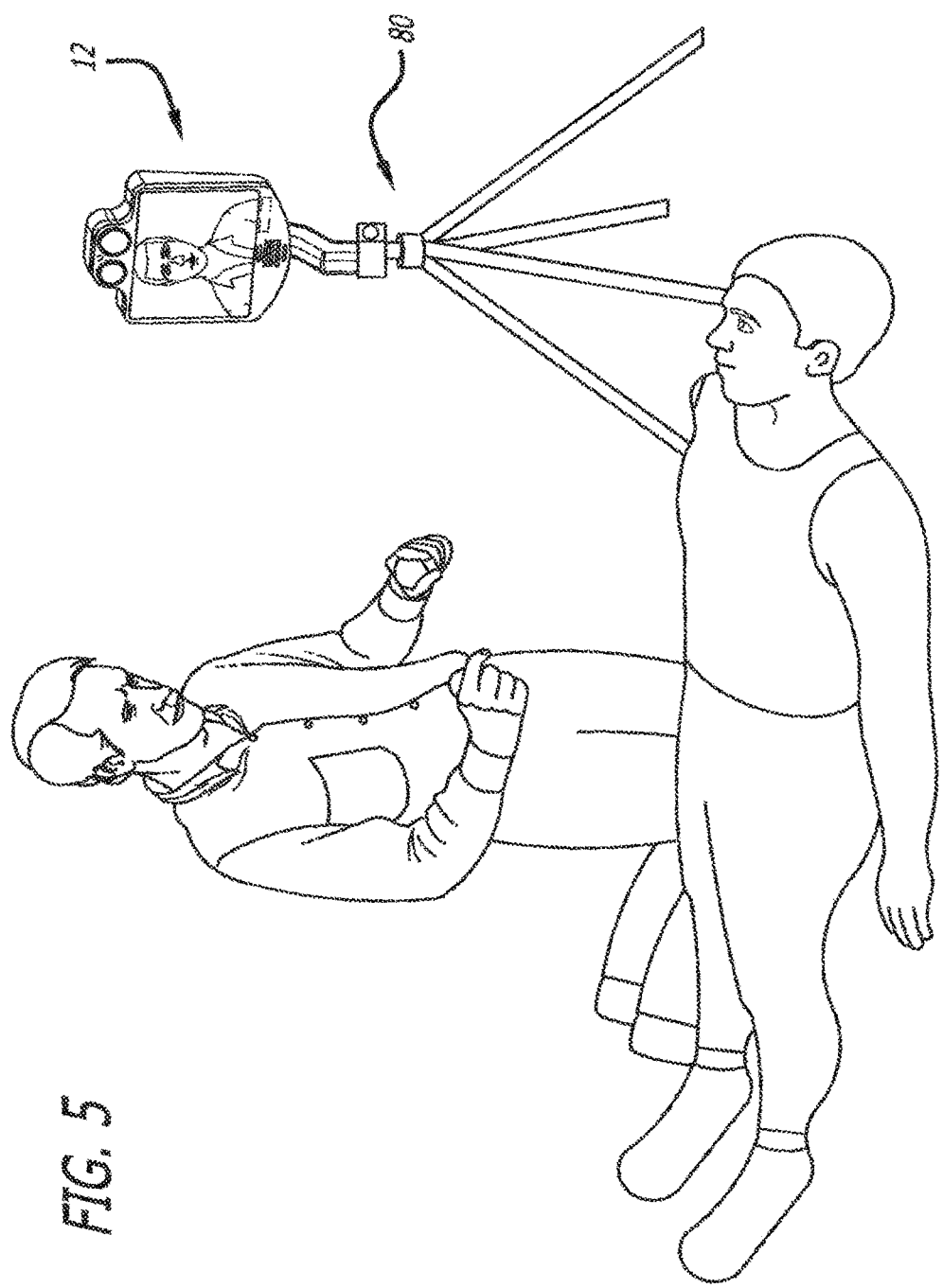
FIG. 5 is an illustration showing the portable robot face attached to a stand.

As shown in FIG. 5 the portable robot face 12 can be detached from the ambulance platform (not shown) and attached to a stand 80 at a remote location. The portable nature of the robot face 12 allows the face 12 to be taken to any location to allow for remote tele-presence of the operator of the remote station. If the operator is a physician the portable robot face 12 allows for remote medical consultation at any site.

Figure 6:
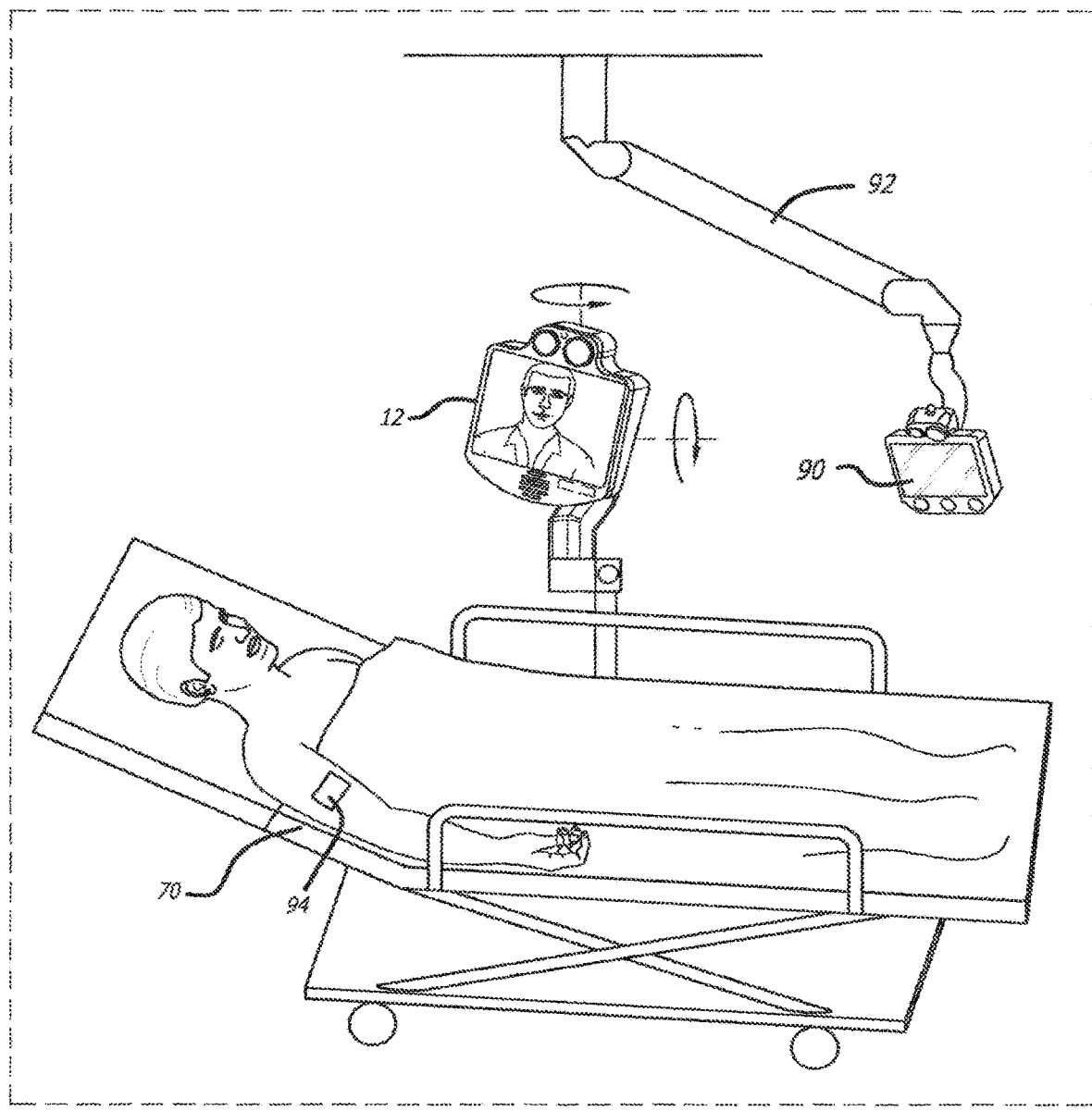
FIG. 6 is an illustration showing a patient within a healthcare facility that has a robot face attached to a boom.

FIG. 6 shows the patient and gurney moved into a healthcare facility with a robot face 90 attached to a boom 92. When the gurney 70 is moved into close proximity with the healthcare facility the robot face wireless transceiver may be coupled to the remote station thru the healthcare facility local wireless network such as a WiFi network. Once inside the facility the portable robot face can be connected to an electrical power outlet and a network for Ethernet connection. An electronic ID device 94 may be attached to the patient. The ID device 94 may transmit a wireless signal to the robot face 90 attached to the boom 92. Receipt of the signal by the face 90 may cause the remote station to be coupled to the robot face 90 attached to the boom 92 instead of the portable robot face 12. The robot face 90 may be coupled to the remote station by other means. For example, a nurse may type in information into the healthcare facility network system that identifies the new location of the patient. Such an entry may cause the system to switch the remote control station to the robot face 90. Additionally, there may be other methodologies for inducing the system to automatically transfer the remote station from one robot to another robot.

FIGS. 7A, 7B and 8 show another embodiment of a portable robot face 100. The face 100 includes a monitor 102, a first camera 104, a microphone 106 and a speaker 108 all attached to a first face 110 of a housing 112. The camera 104 may include a fish eye lens with a 180 degree field of view and a zoom feature. The face 100 is constructed to have a size and weight so that it can be carried by a single human being. The robot face 100 may have a handle 114 to facilitate carrying and moving the device 100. The housing 112 may be constructed so that the face 100 can stand in an upright position on a surface.

The robot face 100 may include a viewfinder screen 116 and a second camera 118 attached to a second face 120 of the housing 112. The second camera 118 can capture images of a person holding the face that are transmitted to the remote station. Located within the housing 112 are electronic circuits and devices, including a processor(s), memory and hard disk drive (not shown) that can perform the various functions of the robot face 100. One side of the face 100 may include various ports 122, 124, 126, 128 and 130. Port 122 may provide a USB and/or Bluetooth connection. The USB port can be used to attach a medical instrument such as a stethoscope or a blood pulse oximeter to the robot face 100. Port 124 may provide C video, S video auxiliary inputs. A battery of the face may be charged through connector 126. A cell phone connection may be established through a transceiver 128 within the housing 112. Connector 130 may provide 801.11 WiFi connectivity. As shown in FIG. 7B, the other side of the face 100 may include different input buttons 132 that can establish videoconferencing controls such as audio volume adjustment. The robot monitor may display the various ports and pluggable devices that can be used with the robot face through touch screens operated by the user.

In certain emergency transport situations, particularly in noisy environments, the remote physician may want to hear everything that is in the area, and simultaneously focus on a single individual providing detailed information. For example, the physician may need to be aware of sounds from the patient, but also focused in on a description of the patient's history given by an on-site technician with a headset. The on-site technician may be using a wired microphone which is plugged in and tethered to the unit, but will more likely be utilizing a BlueTooth headset wirelessly coupled to the unit. The system provides live mixing between the on-board microphone 106, which provides ambient audio of the local environment, and the wireless or tethered microphone (for example a USB headset tethered to port 122). In one embodiment, the control station user interface contains a slider indicating the cross-fade between the two streams. The default position is in the center, but the physician may slide the tab to the left or right to adjust the relative input level of one source to the other.

The system may additionally provide output simultaneously to the unit's on-board speaker 108, and to a paired BlueTooth or tethered headset, for example a USB headset attached to port 122.

The system may run in a variety of modes, shown in the table below, which may be selected by the remote physician, or alternatively by a local caregiver on the unit's interface. In the Normal mode, all inputs and outputs are active and mixed. In Privacy Mode BlueTooth, audio input and output is limited to the BlueTooth headset, while in Privacy Mode Aux, audio input and output is limited to the auxiliary tethered headset. In Mode R, the on-board microphone is disabled, allowing the remote physician to concentrate on the individual with the headset only. In Mode J, the on-board speaker is disabled, allowing the remote physician to hear everything but not disturb others in the environment that are not on a headset. Finally, Mixed BlueTooth mode allows for user-modifiable mixing between the on-board microphone and the BlueTooth microphone, while Mixed Aux mode allows for user-modifiable mixing between the on-board microphone and the auxiliary tethered microphone.

| | INPUTS | | | OUTPUTS | | |
|---|---|---|---|---|---|---|
| Mode | RP-X on-board Mic | BlueTooth In | Aux input (tethered) | RP-X on-board Spkr | BlueTooth Out | Aux/line output |
| Normal | ON | ON | ON | ON | ON | ON |
| Privacy Mode - BlueTooth | off | ON | off | off | ON | off |

| Mode | INPUTS | | | OUTPUTS | | |
| --- | --- | --- | --- | --- | --- | --- |
| | RP-X on-board Mic | BlueTooth In | Aux input (tethered) | RP-X on-board Spkr | BlueTooth Out | Aux/line output |
| Privacy Mode - Aux | off | off | ON | off | off | ON |
| mode R | off | ON | ON | ON | ON | ON |
| mode J | ON | ON | ON | off | ON | ON |
| Mixed - BlueTooth | Percentage | Percentage | off | ON | ON | ON |
| Mixed - Aux | Percentage | off | Percentage | ON | ON | ON |

Figure 9:
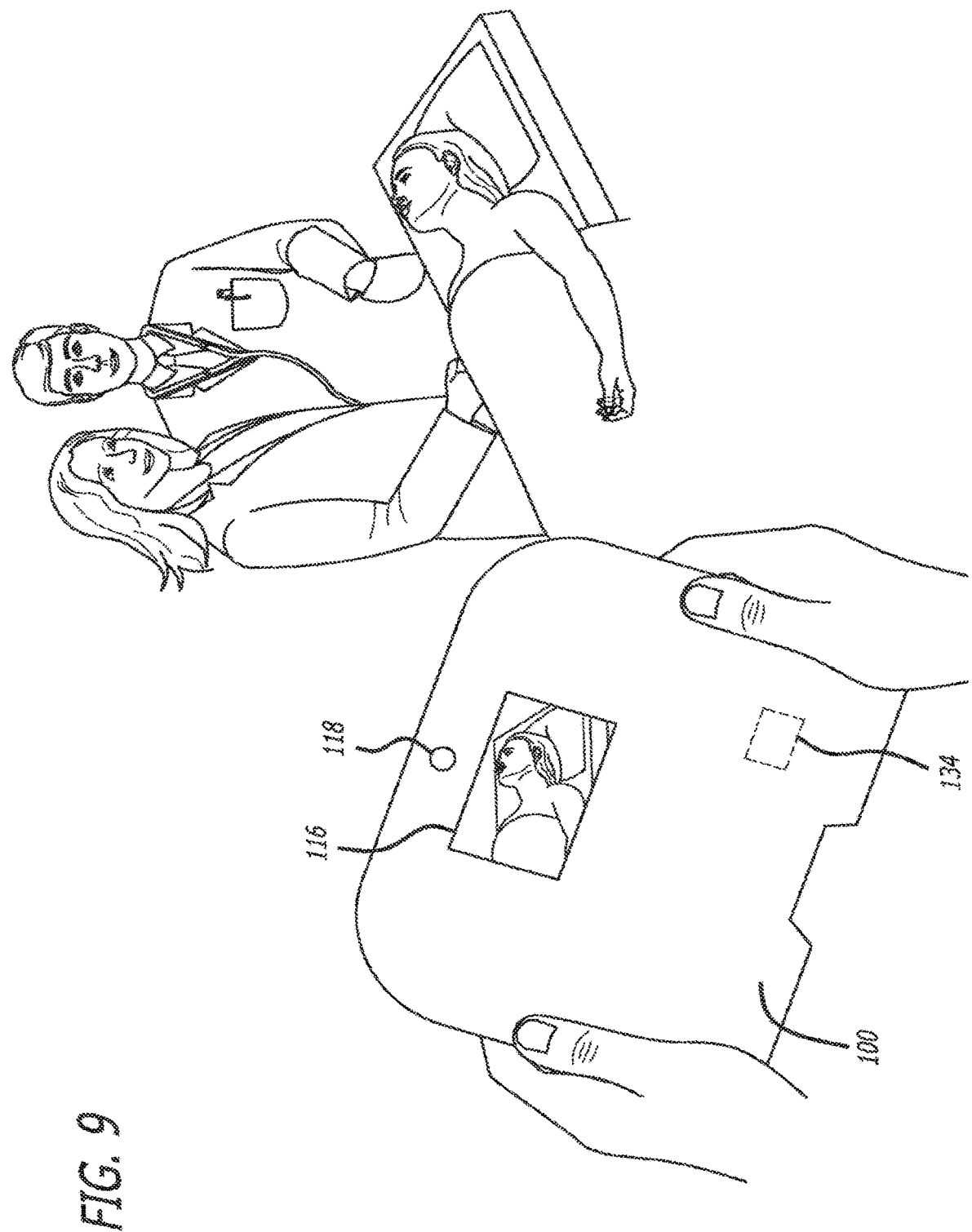
FIG. 9 is an illustration showing a user holding the portable robot face while viewing an image captured by the robot camera through a viewfinder screen.

FIG. 9 shows a user holding the portable robot face 100 to allow a remote operator to view a patient through the first robot camera located on the opposite side of the face. The viewfinder screen 116 allows the holder to view the image being captured by the first robot camera and move the face 100, accordingly. By way of example, the operator at the remote station can provide oral instructions to the holder to move the portable robot face 100 to obtain a desired view of the patient. To this extent the user performs the functions of the actuators shown in FIGS. 2 and 3 and described above.

The robot face 100 may include a motion sensing device 134 such as an accelerometer, gyro and/or magnetometer. The motion sensing device 134 can be utilized so that the person displayed by the robot monitor is right sized even if the user is holding the robot face 100 in a tilted manner. Likewise, the motion sensing device 134 can be used to provide a right sized image to the remote station.

The viewfinder screen 116 may include touch features that allow the holder of the face 100 to change the image being captured. For example, movement of the holder's fingers from an inward location in an outward manner may cause the captured image to be zoomed in. An opposite movement of the user's fingers may cause the image to zoom out.

Figure 10:
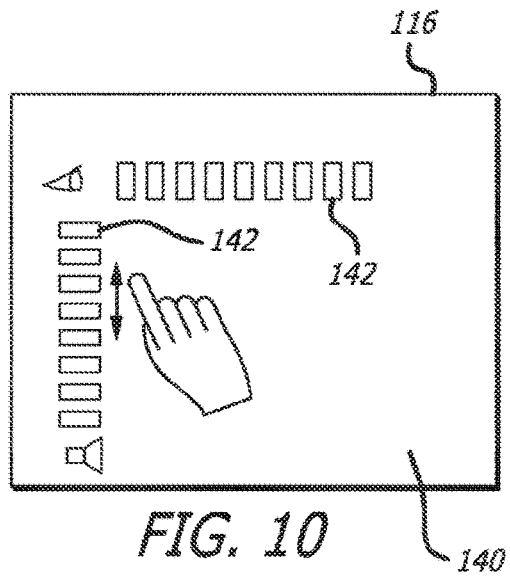
FIG. 10 is an illustration showing a user interface that allows a user to vary speaker and microphone volume.
Figure 11:
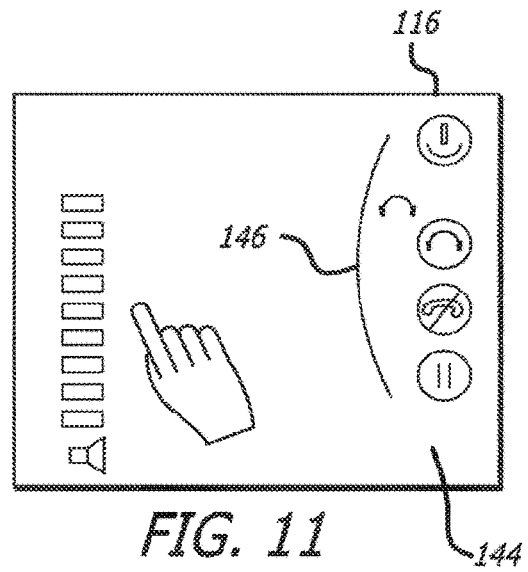
FIG. 11 is an illustration showing a user interface that allows a user to perform certain functions through graphical icons.

FIG. 10 shows a user interface 140 displayed by the viewfinder 116. The interface 140 includes graphical icons 142 that can be touched by the user to change the volume of the robot speaker and microphone. The viewfinder 116 may also display the interface 144 shown in FIG. 11. The interface 144 includes graphical icons 146 that can be touched to control such functions as power, audio modes, connect/disconnect and a hold button.

Figure 12:
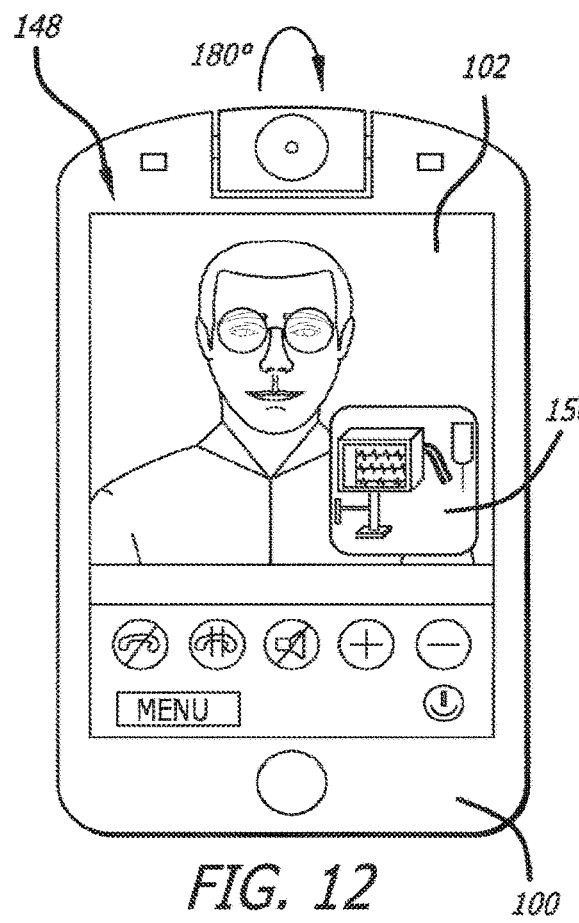
FIG. 12 is an illustration showing a picture in picture display.

FIG. 12 shows the robot monitor 102 displaying an image 148 of the remote operator and the image 150 captured by the robot camera in a picture in picture format.

Figure 13:
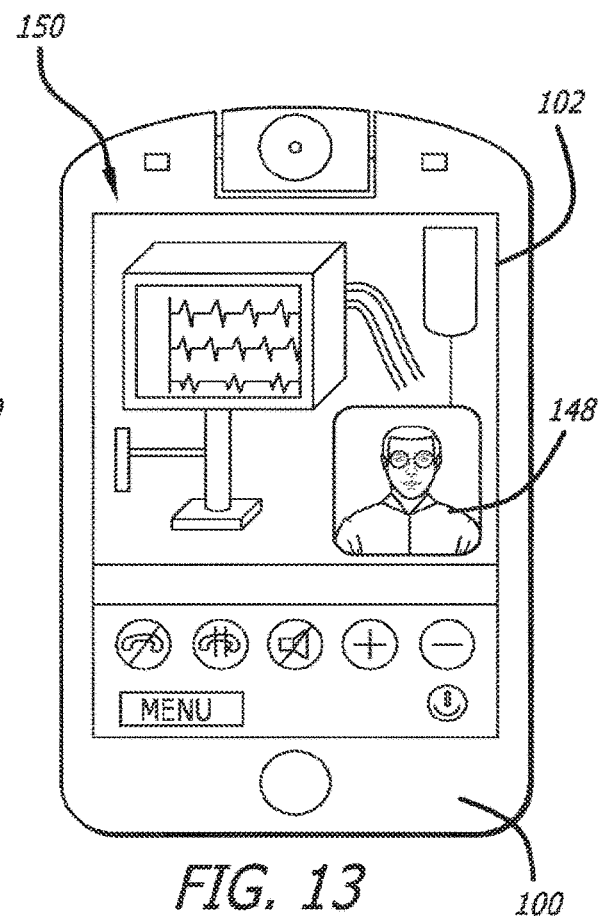
FIG. 13 is an illustration showing the pictures in swapped positions.

The images 148 and 150 can be swapped as shown in FIG. 13. The images can be swapped by a touch screen toggle (not shown) displayed by the viewfinder screen, or by a graphical switch at the remote station.

Figure 14:
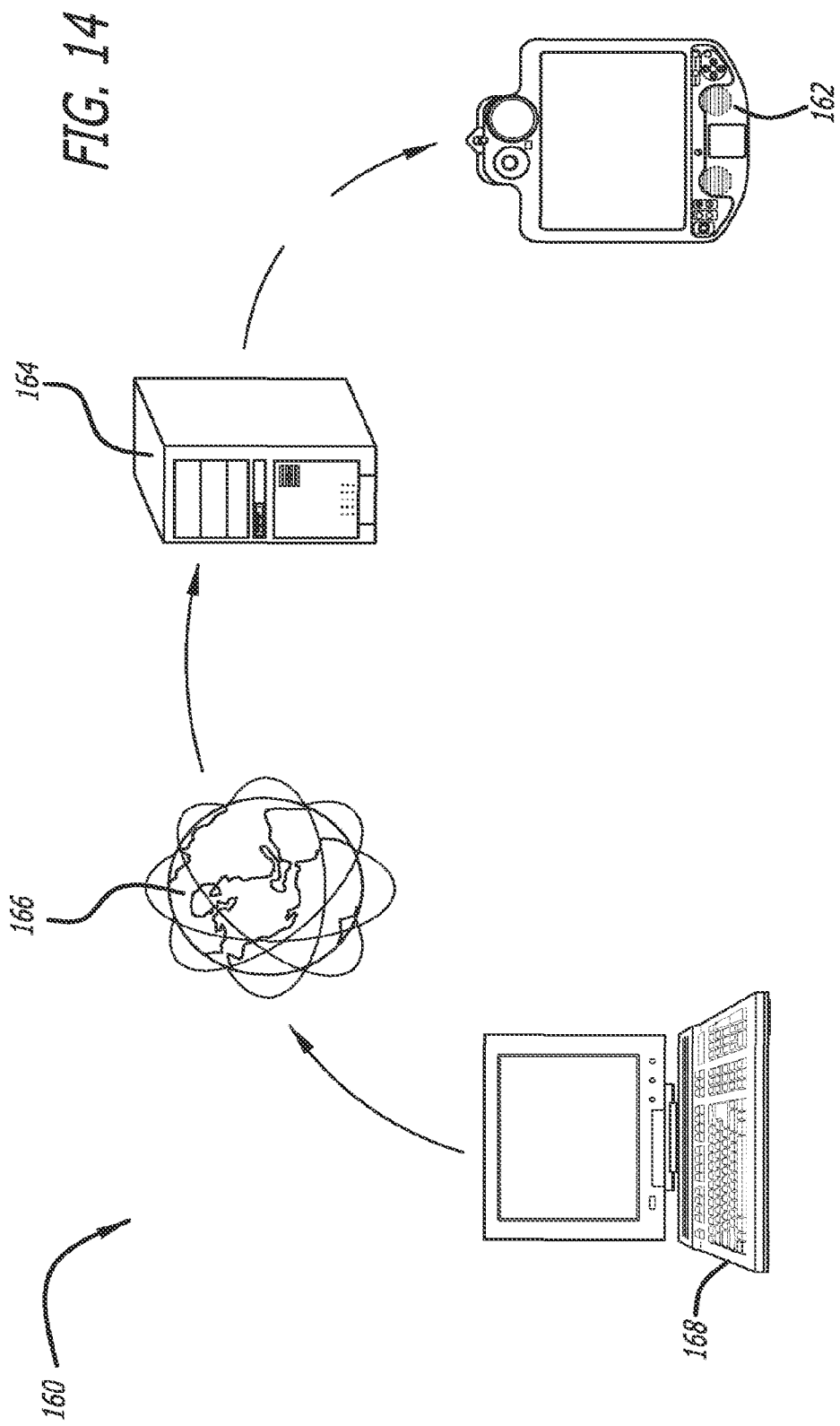
FIG. 14 is an illustration showing a graphical interface showing communication links in the system.

As shown in FIG. 14, the remote device 12 and/or the remote station may provide a graphical interface 160 that shows the connectivity between the robot face and the remote station. Graphical icons 162, 164, 166 and 168 may represent the robot face, a server, the network and remote station, respectively. A solid line between two devices indicates an established link. A broken line indicates a broken communication link between two devices. For example, FIG. 14 depicts a broken communication between the network and remote station. The system can perform diagnostic and corrective action functions for broken links. The corrective actions may be automatic, or include prompt messages to the user to perform certain task such as plugging in their Ethernet cable, or provide instructions to configure a firewall.

Figure 15:
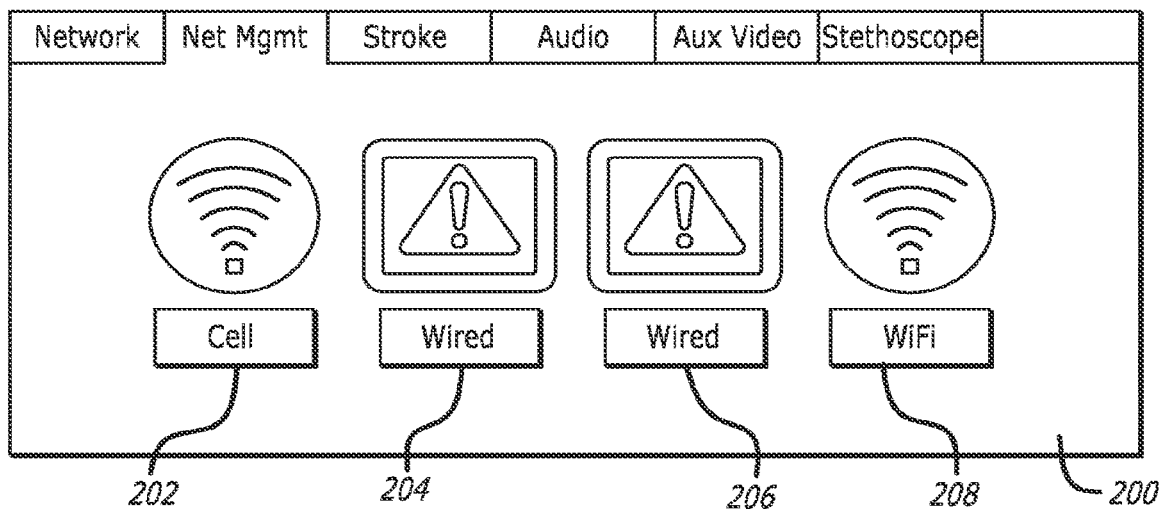
FIG. 15 is an illustration of a graphical interface with a plurality of graphical icons that each represents a different type of communication link between a remote device and its initial node.
Figure 16:
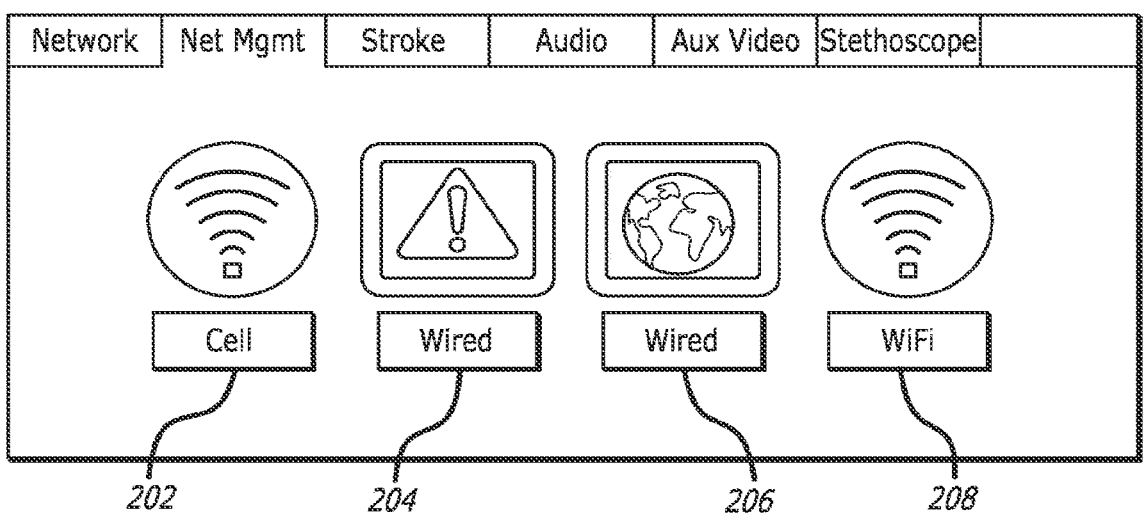
FIG. 16 is an illustration similar to FIG. 14 wherein a graphical icon appearance is changed to indicate the availability of a type of communication link.

FIG. 15 shows a graphical user interface 200 provided by the remote station 14 that displays a plurality of graphical icons 202, 204, 206 and 208. Each icon represents a different type of communication link with the remote device and its initial node. The initial node is the first device in communication with the remote device 12. For example, the initial node may be a cellular tower or an 802.11 access point or other such relay station; or alternatively router, hub, server or other device in a wired connection such as Ethernet. For example, graphical icon 202 may represent a wireless cellular communication link and icon 208 may represent a wireless WiFi link. Icons 204 and 206 may represent wired communication links. The icons can convey whether a type of communication link is available. FIG. 15 shows that the cell and WiFi links are available but the wired links are not available. FIG. 16 shows a change in status wherein a wired communication link with the remote device has become available.

The graphical icons 202, 204, 206 and 208 are selectable so that a user can change the communication link of the remote device. If the user selects a different type of communication link the control station sends a command to the remote device to terminate the present communication session and re-establish communication with the selected communication link. The graphical display 200 allows the remote user to vary communication links. For example, in a situation wherein the remote device is associated with a patient being moved into and through a healthcare facility, a physician at the control station can change the type of communication. For example, the physician may select a cell network when the patient is outside the healthcare facility and then switch to a WiFi connection when the patient is being moved within the facility.

Figure 17:
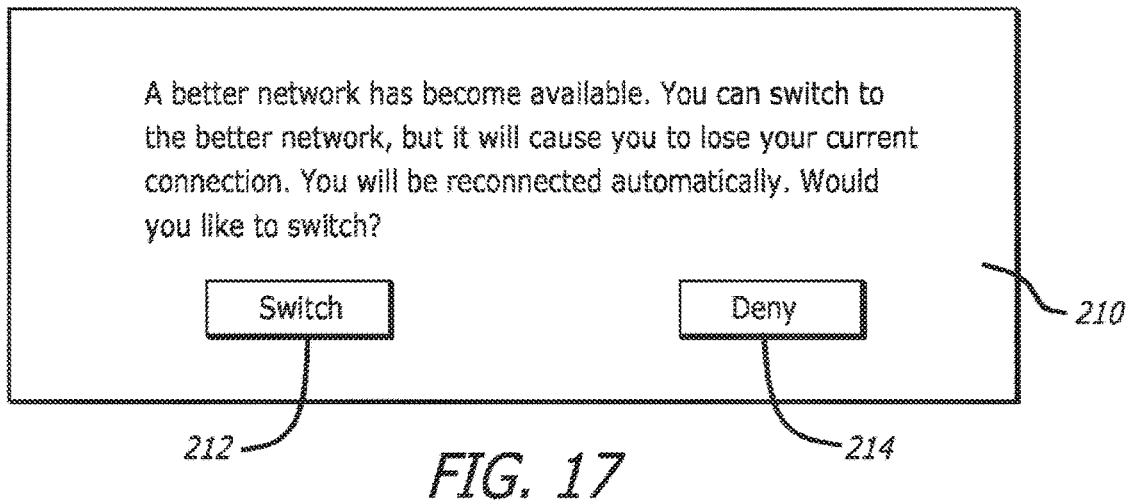
FIG. 17 is an illustration showing a graphical dialog box.
Figures 18A, 18B, 18C:
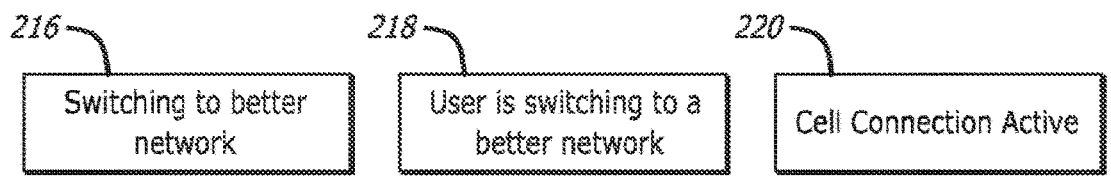
FIGS. 18A-C are illustrations showing message boxes associated with changing the type of a communication link.
Figure 19:
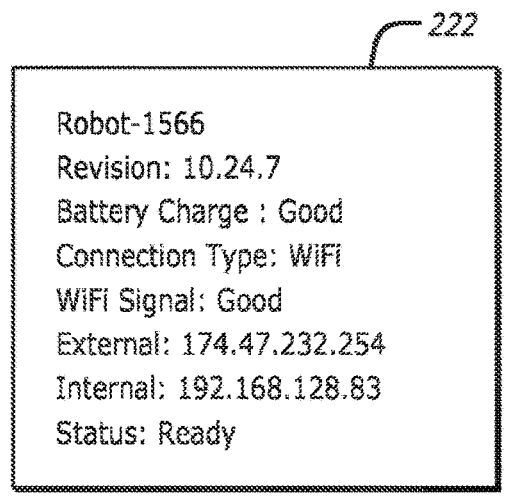
FIG. 19 is an illustration of a message box displayed on the remote device showing a status of a communication link.

The system may evaluate reliability and dynamic bandwidth on each of the network links and determine whether there is a better network link between the remote device and its initial node. If there is a better network link the control station may display the dialogue box 210 shown in FIG. 17. The box 210 may include a message informing the user that there is a better network link. The dialogue box 210 may also have graphical buttons SWITCH 212 and DENY 214 which allow the user to change networks, or not change, respectively. FIG. 18A shows a message box 216 that is displayed at the control station when a network is being switched. FIG. 18B shows a similar message 218 that is displayed at the remote device. FIG. 18C is a message 220 that can be displayed at the control station at the beginning of a communication session when a cell network is the communication link. FIG. 19 shows a display 222 provided by the remote device that conveys information regarding status of the communication link presently utilized by the device.

The portable robot face can be used in various applications. For example, the face 100 can be used to allow for remote examination of a patient. The robot face 100 can remain in an active setup-and-recording mode even when there is no session with a remote operator in progress. This allows for offline recording of patient status, as well as pre-session "setup". Pre-session setup allows a user to position the robot face and use the digital box-zoom controls to ensure optimal viewing of the patient prior to the remote physician's entry. This is to be contrasted with prior art telepresence systems, wherein at the start of a new session, the camera pan/tilt/zoom settings are either at default, or previous settings. The robot face allows a local user can set up the optimal view field for the remote doctor prior to his/her session initiation; and further can update the view field when the remote doctor becomes temporarily busy or requests local assistance.

The robot face 100 may have an "aircraft mode" that inhibits outbound transmission during take-off and landing when the face is located in an aircraft. Additionally, the system may be switched to a "capture-then-send" modality during periods of limited wireless connectivity. In this modality, a user can make a video recording of a patient exam intended for a physician. Exam reports are then automatically forwarded to the physician upon the system regaining adequate connectivity, and placed in a queue at the physician's remote station.

The robot face may also be equipped with a GPS (not shown). This allows for real-time tracking of the geographic location of each face, and geo-tagging of session statistics. This serves a variety of functions, including: analysis of wireless connectivity based on geographic location; tracking of video clips and patient data based on proximity to a hospital and ambulance speed; and hospital and billing auditing.

The portable robot face can be used for various applications in the medical field. One application is specialty transport, in particular pediatric transport. An ambulance and team can be deployed from Hospital A to Hospital B for patient transport. Upon arrival at Hospital B, a patient may be found to be in need of stabilization prior to transport. An expert consultation can occur in Hospital B or during transport on the trip back to Hospital A.

For example, a call may be placed for a transport of a patient from a spoke Hospital B which does not have expertise that Hospital A has (e.g., pediatric intensives specialist care). A transport team from Hospital A is deployed to Hospital B. The team brings the robot face 100, mounts it on a gurney and places the gurney in an ambulance. The team arrives at Hospital B and views the patient. If at any point the transport team would like to request a consult, the remote physician from Hospital A establishes a link with the robot face located on the gurney. The remote physician can pan-tilt-zoom the image to obtain a desired view. If still unable to access the desired views, someone at the robot face side can assist by repositioning the face 100 using the viewfinder to help position the front camera on the patient/desired view. The robot face side team is able to communicate with the remote physician via the main speaker/mic on the unit. The remote physician may speak with various members of the team and patient/family at Hospital B to make a recommendation. In the event of noisy environment, or privacy situation, a Bluetooth headset can be used as an alternative. The remote physician is able to help with decisions regarding care/transport of the patient.

Care can be advanced either through decision to continue transport, to not continue transport, or administer certain care as determined by the remote physician in collaboration with the onsite team. The consult can also occur during transport if there are situations where the patient starts to decompensate. In this case the link would be between a remote station and a robot face located in the ambulance during transport of the patient. The robot would be mounted on a gurney; the remote physician can view the patient and communicate with the transport team to help make a care decision.

Another application may include a nurse conducting a scheduled visit to a chronically ill patient in their home. The nurse views the patient. The touch screen of the face can be used to document various symptoms. The data is stored in the robot. The data and video of certain patient interactions can be forwarded to a server. The robot face may receive requested information from the server. The nurse may observe a troubling symptom and request a physician consult. The nurse may call the physician, who establishes a link with the robot face and initiates a telehealth session with the patient, facilitated by the nurse. The physician may request that the nurse attach a digital stethoscope to the robot face and apply it to the patient. The physician may then request that the nurse attach a portable ultrasound device to the auxiliary video port of the robot face. Finally the physician may decide that the patient should be taken immediately to a medical facility. The nurse may call the ambulance. The nurse stays by the patient's side, with the remote physician logged into the robot face, as the patient is transported to the facility.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

The invention claimed is:

1. A communication system comprising:
a first device at a first location that establishes a communication session with a second device at a second location through at least an initial node, each of the first and second devices has a camera, a monitor, a speaker and a microphone, wherein, during the communication session, the monitor of the first device displays a graphical interface including a plurality of graphical icons that each represent a different type of communication link between the second device and the initial node, and wherein the graphical icons are selectable to change the type of communication link between the second device and the initial node and the graphical interface is not displayed on the monitor of the first device.

2. The first device of claim 1, wherein the graphical icons display whether a type of communication link is available.

3. The first device of claim 1, wherein a graphical dialog box is displayed that informs a user that an alternative type of communication is available and allows the user to select the alternative type of communication.

4. A telepresence system, comprising:
a first device at a first location, the first device includes a camera, a monitor, a speaker and a microphone; and,
a second device at a second location, the second device includes a camera, a monitor, a speaker and a microphone, wherein the first device establishes a communication session with the second device through at least an initial node and, during the communication session, the monitor of the first device displays a graphical interface including a plurality of graphical icons that each represent a different type of communication link between the second device and the initial node, and wherein the graphical interface is not displayed on the monitor of the first device.

5. The system of claim 4, wherein the graphical icons are selectable to change the type of communication link.

6. The system of claim 4, wherein the graphical icons display whether a type of communication link is available.

7. The system of claim 4, wherein a graphical dialog box is displayed that informs a user that an alternative type of communication is available and allows the user to selected the alternative type of communication.

8. A method for communicating between a first device at a first location and a second device at a second location, the first device and the second device are coupled by at least an initial node, the method comprising:

establishing a communication session with the second device;

transmitting an image captured by a camera of the first device to the second device;

displaying an image captured by a camera of the second device on a monitor of the first device;

transmitting an audio instruction captured by a microphone of the first device to the second device; and, displaying, on a monitor of the first device, a graphical interface including a plurality of graphical icons that each represent a different type of communication link between the second device and the initial node without displaying the graphical interface on the monitor of the second device.

9. The method of claim 8, further comprising selecting one of the graphical icons to change the type of communication link.

10. The method of claim 8, wherein the graphical icon is selected while a user of the second device is moving with a patient through a healthcare facility.

11. The method of claim 8, wherein the graphical icons display whether a type of communication link is available.

12. The method of claim 8, further comprising displaying a graphical dialog box that informs a user that an alternative type of communication is available, and selecting the alternative type of communication.

* * * * *